United States Patent
Ragosta

(10) Patent No.: US 11,020,138 B2
(45) Date of Patent: Jun. 1, 2021

(54) PUSH-PULL SURGICAL INSTRUMENT END EFFECTOR ACTUATION USING FLEXIBLE TENSION MEMBER

(71) Applicant: Intuitive Surgical Operations, Inc., Sunnyvale, CA (US)

(72) Inventor: Nicholas Ragosta, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 185 days.

(21) Appl. No.: 16/331,734

(22) PCT Filed: Sep. 8, 2017

(86) PCT No.: PCT/US2017/050760
§ 371 (c)(1),
(2) Date: Mar. 8, 2019

(87) PCT Pub. No.: WO2018/049217
PCT Pub. Date: Mar. 15, 2018

(65) Prior Publication Data
US 2019/0201150 A1    Jul. 4, 2019

Related U.S. Application Data

(60) Provisional application No. 62/385,642, filed on Sep. 9, 2016.

(51) Int. Cl.
*A61B 17/29*    (2006.01)

(52) U.S. Cl.
CPC ...... *A61B 17/29* (2013.01); *A61B 2017/2902* (2013.01); *A61B 2017/2932* (2013.01)

(58) Field of Classification Search
CPC ............. A61B 17/00234; A61B 17/29; A61B 17/2902; A61B 17/2932;
(Continued)

(56) References Cited

U.S. PATENT DOCUMENTS

| 7,951,165 B2 | 5/2011 | Golden et al. |
| 8,105,320 B2 | 1/2012 | Scott et al. |

(Continued)

FOREIGN PATENT DOCUMENTS

| CN | 103930056 A | 7/2014 |
| CN | 105163679 A | 12/2015 |

(Continued)

OTHER PUBLICATIONS

Extended European Search Report for Application No. EP17849648.6, dated Apr. 9, 2020, 9 pages.

(Continued)

*Primary Examiner* — Melanie R Tyson
(74) *Attorney, Agent, or Firm* — Kilpatrick Townsend & Stockton LLP

(57) ABSTRACT

Surgical tools and related methods articulate an actuation rod assembly via an actuation tension member. A surgical tool includes an end effector, an instrument shaft assembly supporting the end effector, an actuation rod assembly drivingly coupled with the end effector, a guide surface, a flexible tension member connected to the actuation rod assembly, and an actuation portion. The actuation rod assembly is mounted to slide within the instrument shaft assembly. The flexible tension member is connected to the actuation rod assembly at a connection. The flexible tension member includes a first portion that extends distally from the connection to the guide surface, is wrapped around the guide surface, and extends proximally from the guide surface. The actuation portion is drivingly coupled with the flexible tension member and operable to articulate the tension member to articulate the actuation rod assembly to actuate the end effector.

20 Claims, 12 Drawing Sheets

(58) Field of Classification Search
CPC .. A61B 2017/2902; A61B 2017/00477; A61B 34/30; A61B 34/71
See application file for complete search history.

(56) References Cited

U.S. PATENT DOCUMENTS

| | | |
|---|---|---|
| 2003/0135204 A1 | 7/2003 | Lee et al. |
| 2007/0066986 A1 | 3/2007 | Sanchez |
| 2008/0111513 A1 | 5/2008 | Farritor et al. |
| 2010/0076461 A1 | 3/2010 | Viola et al. |
| 2010/0249818 A1 | 9/2010 | Jinno et al. |
| 2011/0230875 A1 | 9/2011 | Walberg et al. |
| 2015/0352715 A1 | 12/2015 | Yanagihara et al. |
| 2016/0022298 A1 | 1/2016 | Parihar et al. |

FOREIGN PATENT DOCUMENTS

| | | |
|---|---|---|
| WO | WO-2015125955 A1 | 8/2015 |
| WO | WO-2016067436 A1 | 5/2016 |

OTHER PUBLICATIONS

International Search Report and Written Opinion for Application No. PCT/US2017/050760, dated Dec. 14, 2017, 11 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

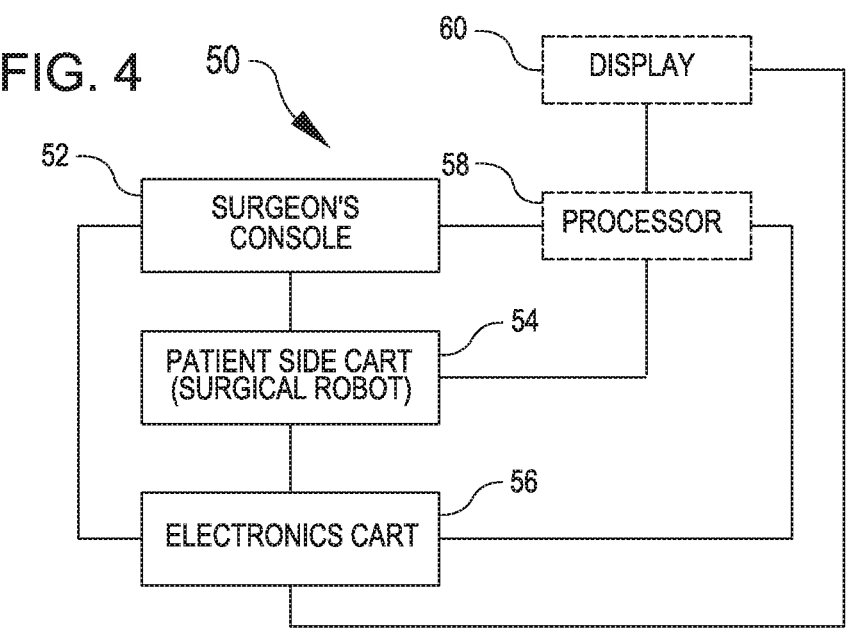
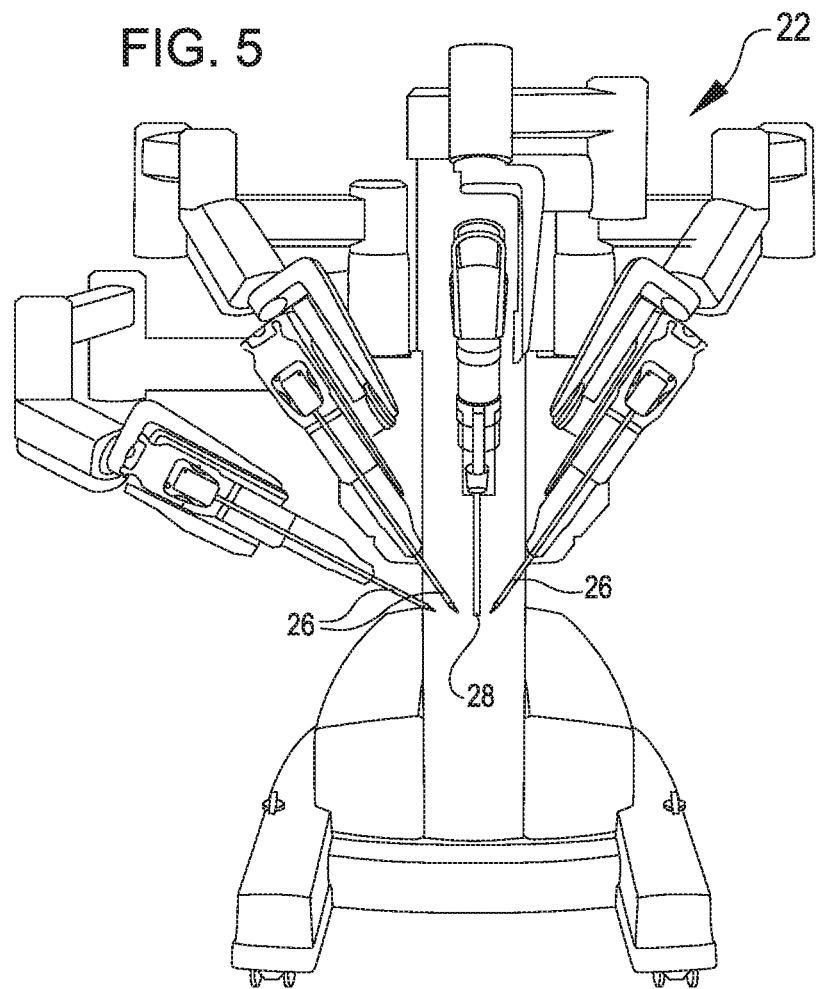

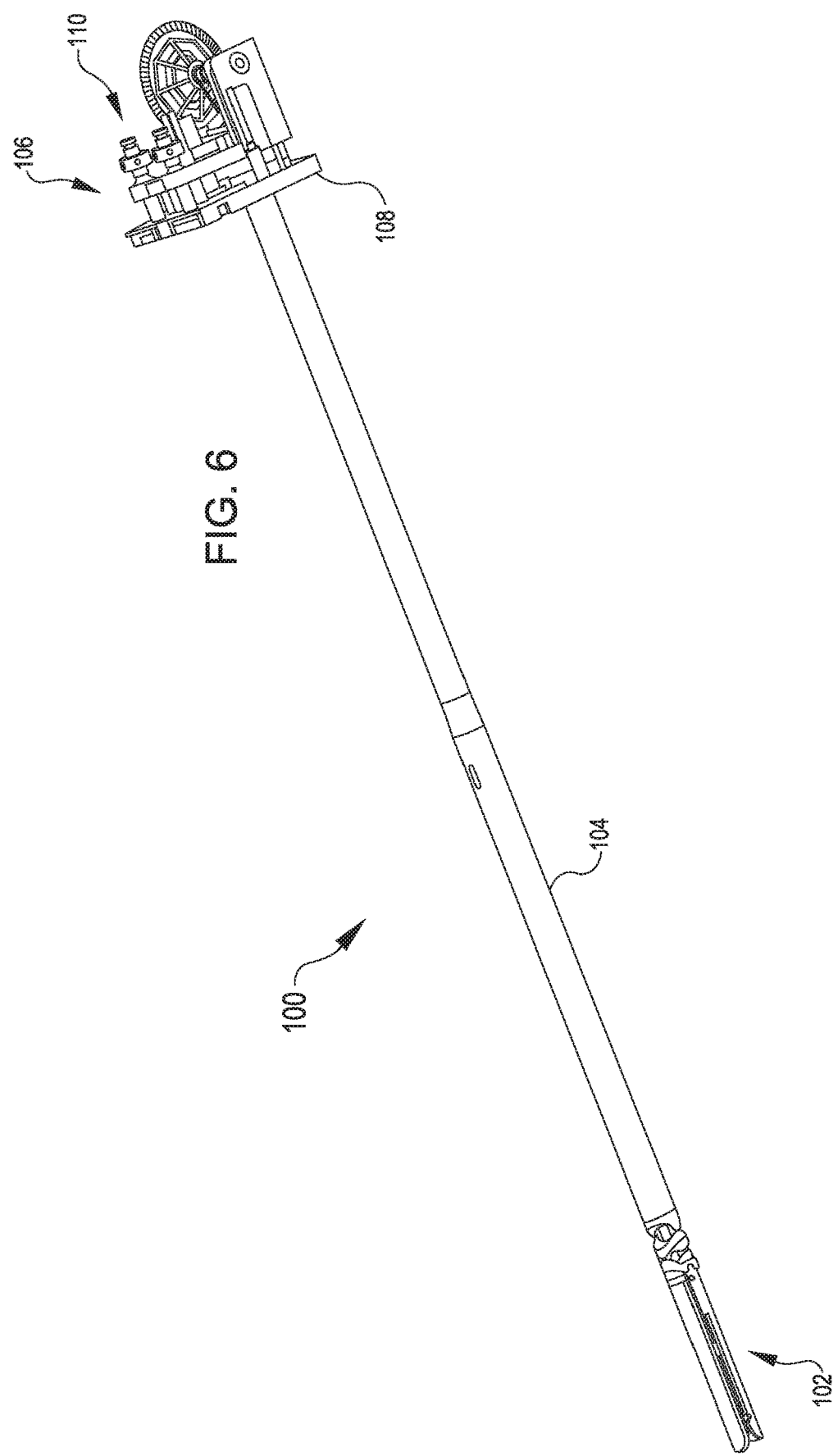

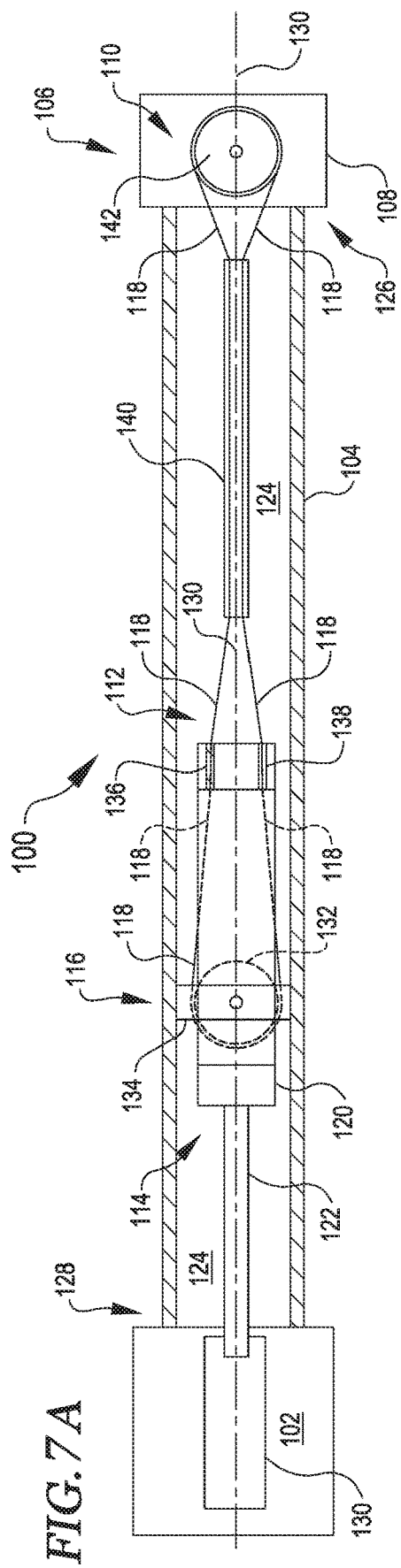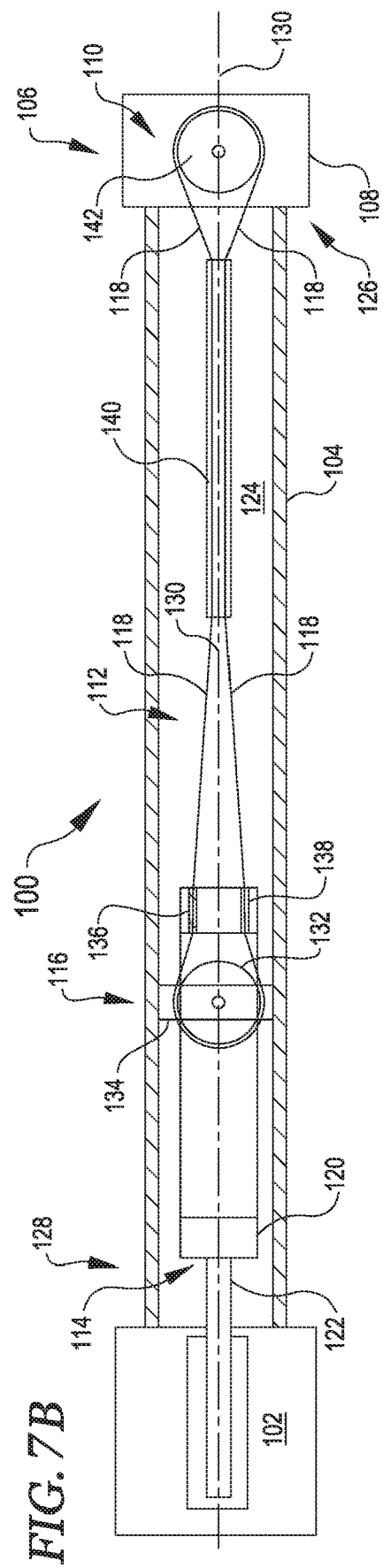

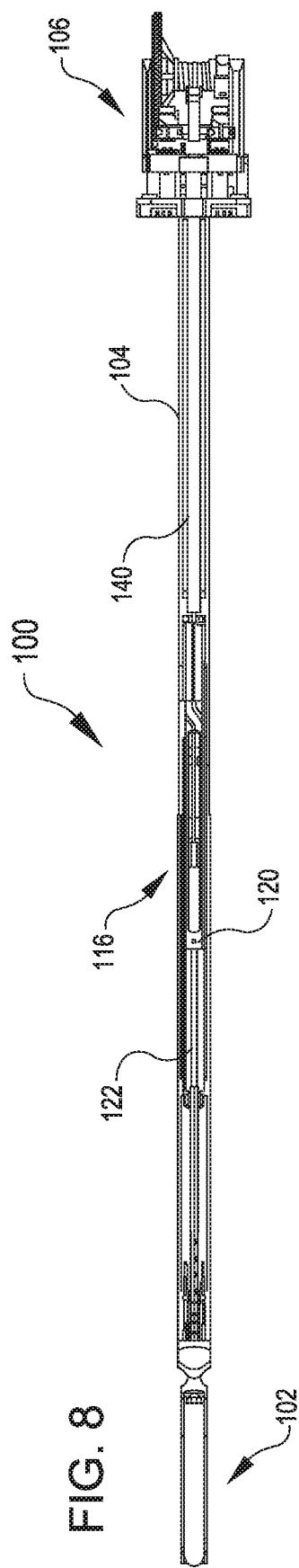
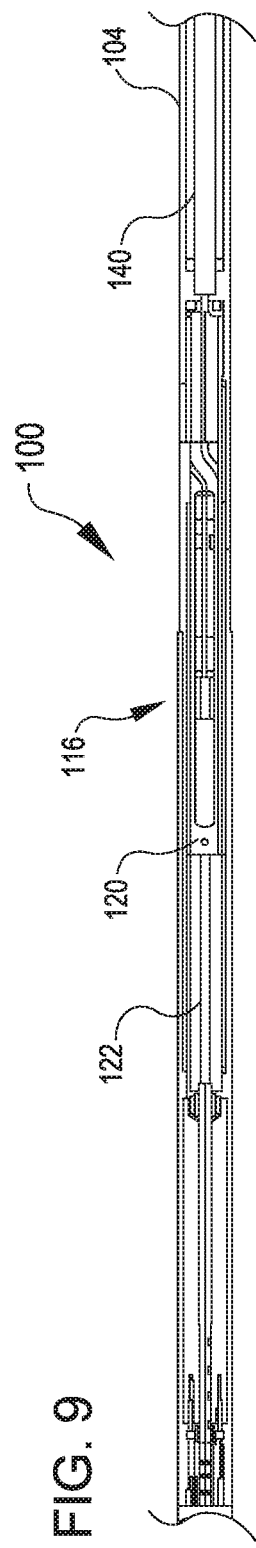
FIG. 8
FIG. 9

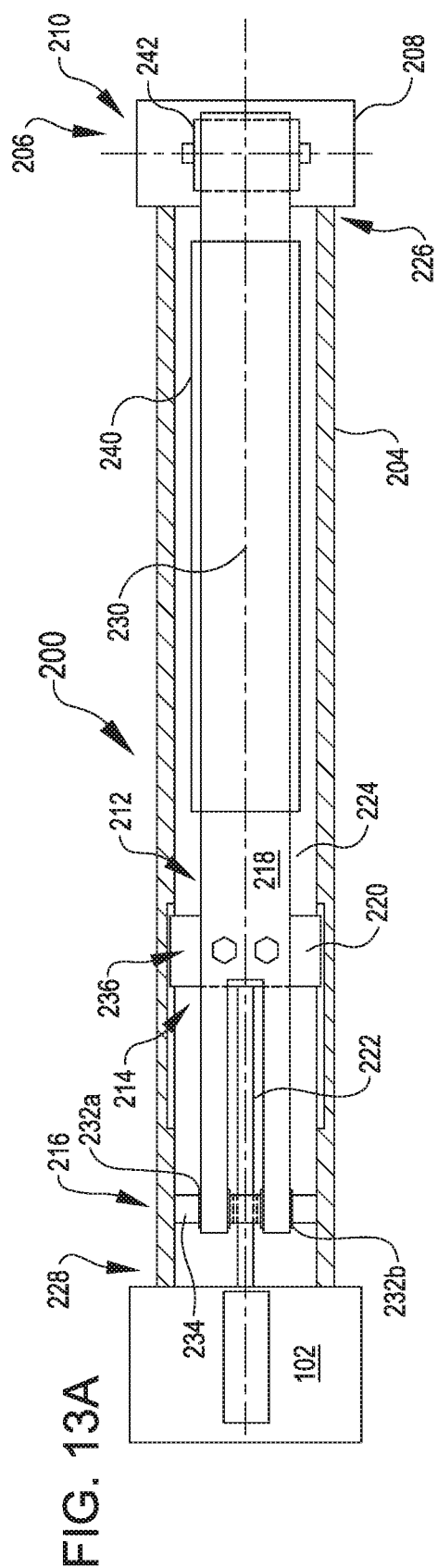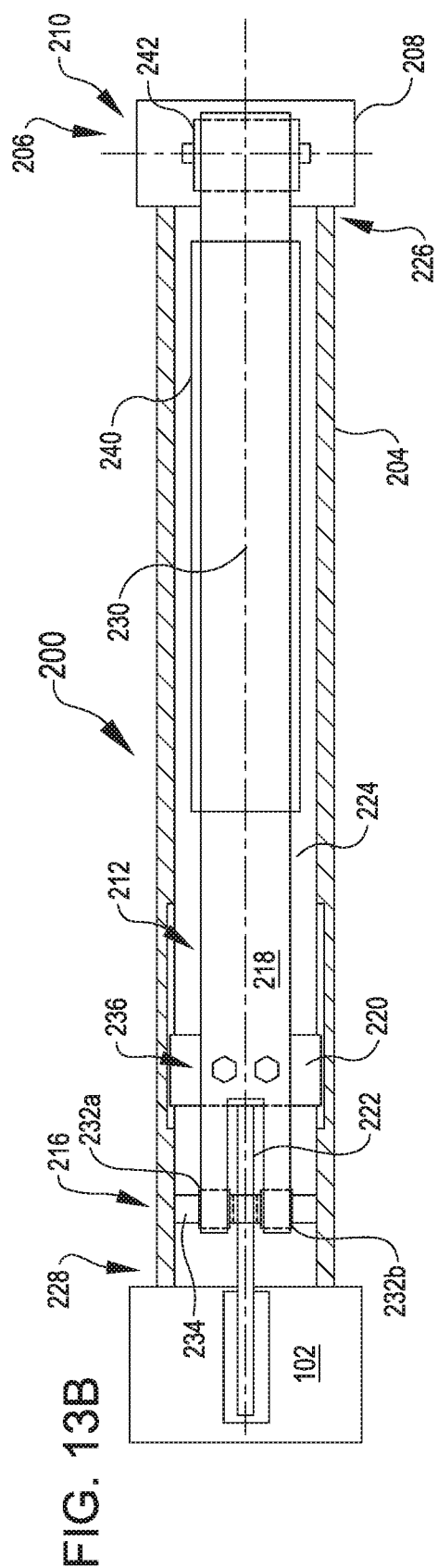

PUSH-PULL SURGICAL INSTRUMENT END EFFECTOR ACTUATION USING FLEXIBLE TENSION MEMBER

CROSS REFERENCE TO RELATED APPLICATION DATA

The present application is a U.S. National Stage Application of PCT/US2017/050760 filed Sep. 8, 2017; which claims the benefit of U.S. Provisional Appln. No. 62/385,642 filed Sep. 9, 2016; the full disclosures which are incorporated herein by reference in their entirety for all purposes.

BACKGROUND

Minimally invasive surgical techniques are aimed at reducing the amount of extraneous tissue damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Surgical clamping and cutting tools (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

A surgical clamping and cutting tool can include an instrument shaft supported end effector to which a replaceable stapler cartridge is mounted. A jaw of the end effector can be articulated to clamp tissue between the stapler cartridge and the jaw. The stapler cartridge can then be articulated to deploy staples from the stapler cartridge to staple tissue clamped between the stapler cartridge and the jaw. The stapler cartridge can include a knife that is articulable to cut the stapled tissue between rows of deployed staples.

The actuation force levels sufficient to clamp, staple, and/or cut tissue can be significant. Moreover, it is desirable to limit the diameter of an instrument shaft supporting the end effector and to actuate the end effector via a proximal actuation portion that is drivingly coupled with the end effector via a linkage extending through the instrument shaft. It is also desirable that a linkage extending through a small diameter instrument shaft to drivingly coupled an end effector with a proximal actuation portion be robust, affordable, and reliable. The surgical tools and related methods presented herein are suitable to transfer sufficient actuation forces to an end effector, such as a clamping, stapling, and cutting end effector through a relatively small-diameter instrument shaft in a robust, affordable, and reliable manner.

BRIEF SUMMARY

Surgical tools and related methods are provided in which proximal retraction of a flexible tension member is used to transfer a distally-directed actuation force through an instrument shaft assembly to an end effector supported by the instrument shaft assembly. The flexible tension member is wrapped around a guide surface disposed within the instrument shaft assembly and connected to an actuation rod assembly that is moved toward the end effector in response to the retraction of the flexible tension member. The actuation rod assembly, the guide surface, and the flexible tension member are configured to be enclosed within an elongated, relatively small-diameter instrument shaft assembly and to transfer a distally-directed actuation force to actuate a surgical end effector, such as a clamping, stapling, and cutting surgical end effector.

Thus, in one aspect, a surgical tool is provided. The surgical tool includes an actuation portion, an end effector, an instrument shaft assembly coupling the actuation portion to the end effector, an actuation rod assembly drivingly coupled with the end effector, and a flexible tension member. The instrument shaft assembly is elongated along an instrument shaft axis and defines a lumen. The instrument shaft assembly includes a guide surface disposed towards a distal end of the lumen. The actuation rod assembly is slideably mounted within the lumen for translation relative to the instrument shaft assembly along the instrument shaft axis. The flexible tension member drivingly couples the actuation portion to the actuation rod assembly. The flexible tension member is connected to the actuation rod assembly at a connection that is longitudinally disposed between the actuation portion and the guide surface. The flexible tension member includes a first portion that, from the connection, extends distally towards the guide surface, wraps around the guide surface, and extends proximally towards the actuation portion. The actuation portion is operable to increase tension in the first portion of the flexible tension member to translate the actuation rod assembly in a distal direction.

In many embodiments, the actuation portion is operable to rotate the instrument shaft assembly around the instrument shaft axis relative to a proximal chassis supporting the instrument shaft assembly. In many embodiments, the actuation rod assembly is constrained to rotate with the instrument shaft assembly around the instrument shaft axis. The surgical tool can include an isolation tube extending along the instrument shaft axis. The isolation tube can be disposed between the connection and the actuation portion. The first and second portions of the flexible tension member can pass through the isolation tube. The isolation tube can enclose an inter-twistable length of the first and second portions and isolate the inter-twistable length from a region of the lumen surrounding the isolation tube. Accordingly, one or more additional actuation members for actuating and/or articulating the end effector can be routed through the region of the lumen surrounding the isolation tube and thereby be kept from being detrimentally impacted as a result of inter-twisting of the first and second portions resulting from rotation of the instrument shaft assembly.

The flexible tension member can include any suitable flexible tension member. For example, the flexible tension member can include an actuation cable. The first portion of the flexible tension member can include a first length of cable and the second portion of the flexible tension member can include a second length of cable. The surgical tool can include a pulley that includes the guide surface. The actuation portion can be operable to move the actuation rod assembly through a range of movement relative to the pulley. The actuation rod assembly can include a slot configured to accommodate the pulley throughout the range of movement. The actuation rod assembly can include a cable guide aperture through which the second length of cable extends.

In many embodiments, the instrument shaft assembly includes separate components (e.g., separate upper and lower half segments) that accommodate installation of the actuation rod assembly, the guide surface, and the flexible tension member into the lumen of the instrument shaft assembly, and joinable to form the lumen enclosing the actuation rod assembly, the guide surface, and the flexible tension member. For example, the instrument shaft assembly can include a first component and a second component. The first and second components can be configured to accommodate insertion of the actuation rod assembly, the guide surface, and the flexible tension member into the lumen when the first and second components are uncoupled. The first and second components can be configured to be joined to form the lumen.

In many embodiments, the actuation portion is operable to move the actuation rod assembly through a range of movement relative to the guide surface. The actuation rod assembly can include a first guide feature that protrudes in a first direction and a second guide feature protrudes in a second direction different than the first direction. The first component and the second component can form a first slot sized to accommodate the first guide feature and a second slot sized to accommodate the second guide feature throughout the range of movement.

The flexible tension member can include suitable flexible tension members other than a cable. For example, the flexible tension member can include a drive band. The drive band can include a slot through which a portion of the actuation rod assembly between the connection and the end effector extends. The surgical tool can include a support frame, a first bearing, and a second bearing. The support frame can have an aperture through which the portion of the actuation rod assembly between the connection and the end effector extends. The first bearing can be mounted to the support frame to rotate around a guide surface axis perpendicular to the instrument shaft axis and interface with the drive band on a first side of the slot. The second bearing can be mounted to the support frame to rotate around the guide surface axis and interface with the drive band on a second side of the slot opposite to the first side of the slot. The actuation rod assembly can include a drive band guide aperture through which the drive band extends.

In another aspect, a method is provided for actuating an end effector of a surgical tool. The method includes supporting an end effector via an instrument shaft assembly elongated along an instrument shaft axis, enclosing an actuation rod assembly within a lumen of the instrument shaft assembly, guiding the actuation rod assembly during movement of the actuation rod assembly along the instrument shaft axis, and operating an actuation portion to increase tension in a first portion of a flexible tension member drivingly coupled with the actuation rod assembly to move the actuation rod assembly toward the end effector to actuate the end effector. The first portion of the flexible tension member extends distally from the actuation portion to a guide surface, is wrapped around the guide surface, and extends from the guide surface to a connection between the first portion of the flexible tension member and the actuation rod assembly. In many embodiments, the method further includes operating the actuation portion to increase tension in a second portion of the flexible tension member drivingly coupled with the actuation rod assembly to move the actuation rod assembly away from the end effector.

In many embodiments, the method includes operating the actuation portion to rotate the instrument shaft assembly around the instrument shaft axis relative to a proximal chassis supporting the instrument shaft assembly. The method can include constraining the actuation rod assembly to rotate with the instrument shaft assembly around the instrument shaft axis. The method can include enclosing an inter-twistable length of the first and second portions of the flexible tension member disposed between the actuation rod assembly and the actuation portion within an isolation tube to isolate the inter-twistable length from a region of the lumen surrounding the isolation tube.

In many embodiments of the method, the flexible tension member includes a cable. For example, the first portion of the flexible tension member can include a first length of cable. The second portion of the flexible tension member can include a second length of cable. The surgical tool can include a pulley that includes the guide surface. The method can include operating the actuation portion to move the actuation rod assembly through a range of movement relative to the pulley and accommodating the pulley within a slot of the actuation rod assembly throughout the range of movement. The method can include guiding the second length of cable via a cable guide aperture in the actuation rod assembly through which the second length of cable extends.

In many embodiments of the method, the instrument shaft assembly includes separate components (e.g., separate upper and lower half segments) that accommodate installation of the actuation rod assembly, the guide surface, and the flexible tension member into the lumen of the instrument shaft assembly, and joinable to form the lumen enclosing the actuation rod assembly, the guide surface, and the flexible tension member. For example, the method can include inserting the actuation rod assembly, the guide surface, and the flexible tension member into a first component of the instrument shaft assembly and coupling a second component of the instrument shaft assembly to the first component to enclose the actuation rod assembly, the guide surface, and a portion of the flexible tension member within the lumen of the instrument shaft assembly.

In many embodiments, the method includes operating the actuation portion to move the actuation rod assembly through a range of movement relative to the guide surface. The method can include interfacing protruding guide features of the actuation rod assembly with the instrument shaft assembly to guide movement of the actuation rod assembly relative to the instrument shaft assembly through the range of movement.

In many embodiments of the method, the flexible tension member can include suitable flexible tension members other than a cable. For example, the flexible tension member can include a drive band. The method can include accommodating a portion of the actuation rod assembly between the connection and the end effector through a slot in the drive band. The method can include accommodating a portion of the actuation rod extending between the connection and the end effector in an aperture of a support frame, supporting a first bearing mounted to the support frame to rotate around a guide surface axis perpendicular to the instrument shaft axis and interface with the drive band on a first side of the slot, and supporting a second bearing mounted to the support frame to rotate around the guide surface axis and interface with the drive band on a second side of the slot opposite to the first side of the slot. In many embodiments, the first and second bearings include the guide surface. The method can include guiding the drive band via a drive band guide aperture of the actuation rod assembly through which the drive band extends.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 4 diagrammatically illustrates a robotic surgery system, in accordance with many embodiments.

FIG. 5 is a front view of a patient side cart (surgical robot) of a robotic surgery system, in accordance with many embodiments.

FIG. 6 shows a robotic surgical tool, in accordance with many embodiments.

FIG. 7A and FIG. 7B are simplified schematic diagrams illustrating a surgical tool that includes an end effector and a cable-driven mechanism for transferring push/pull actuation forces to the end effector, in accordance with many embodiments.

FIG. 8 is a plan view of an embodiment of the surgical tool of FIG. 7A and FIG. 7B.

FIG. 9 is a plan view showing components of the cable-driven mechanism for transferring push/pull actuation forces to the end effector of the surgical tool of FIG. 8.

FIG. 13A and FIG. 13B are simplified schematic diagrams illustrating a surgical tool that includes an end effector and a band-driven mechanism for transferring push/pull actuation forces to the end effector, in accordance with many embodiments.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
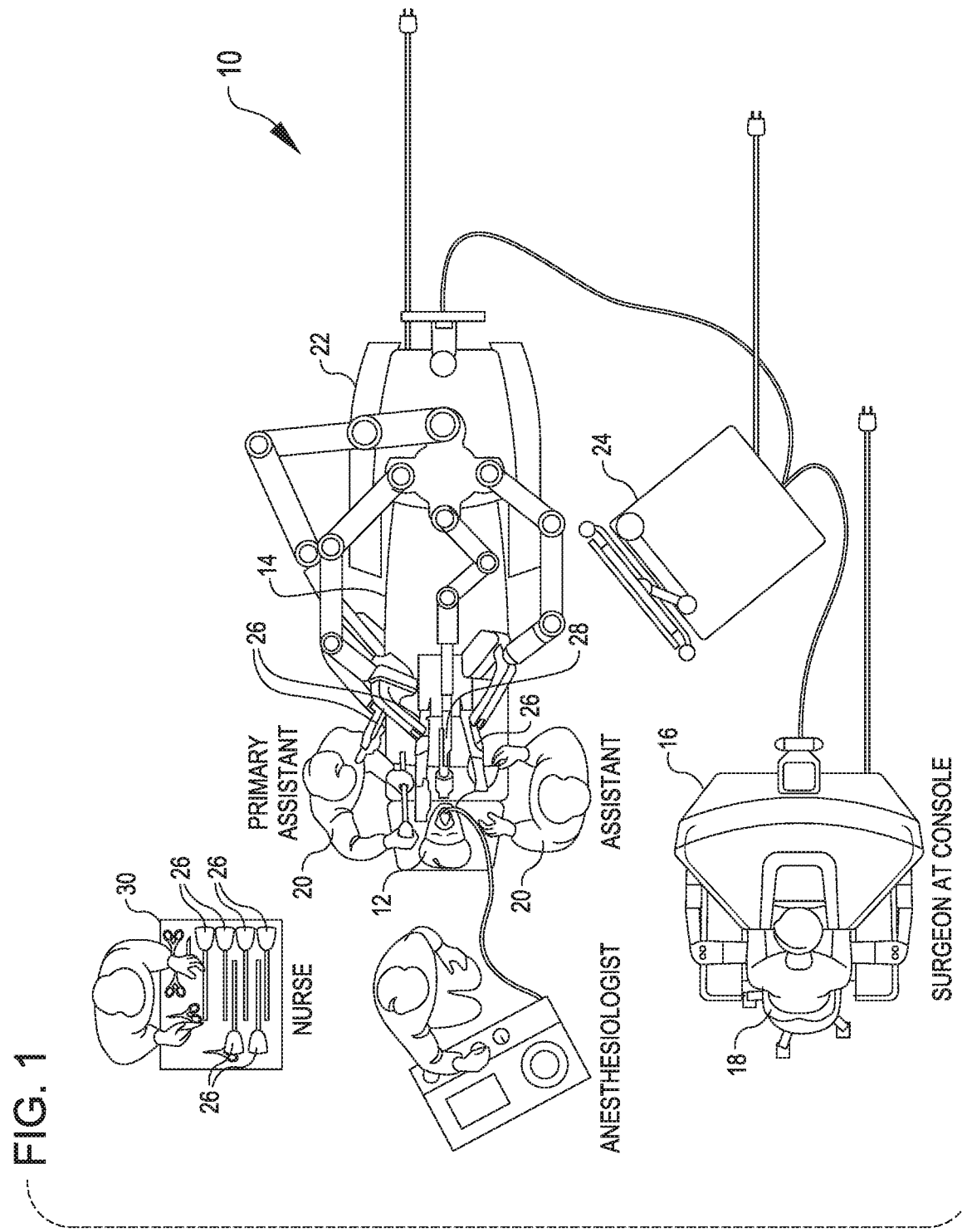
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
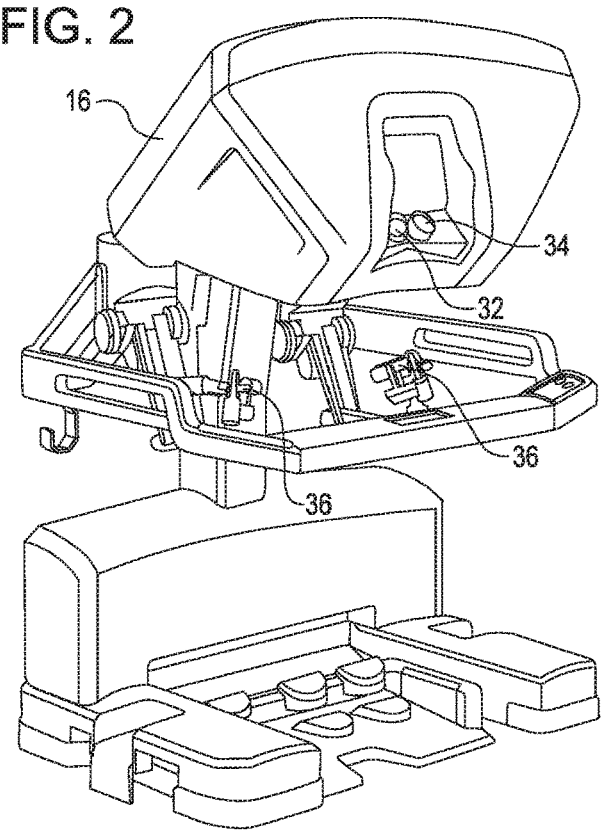
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
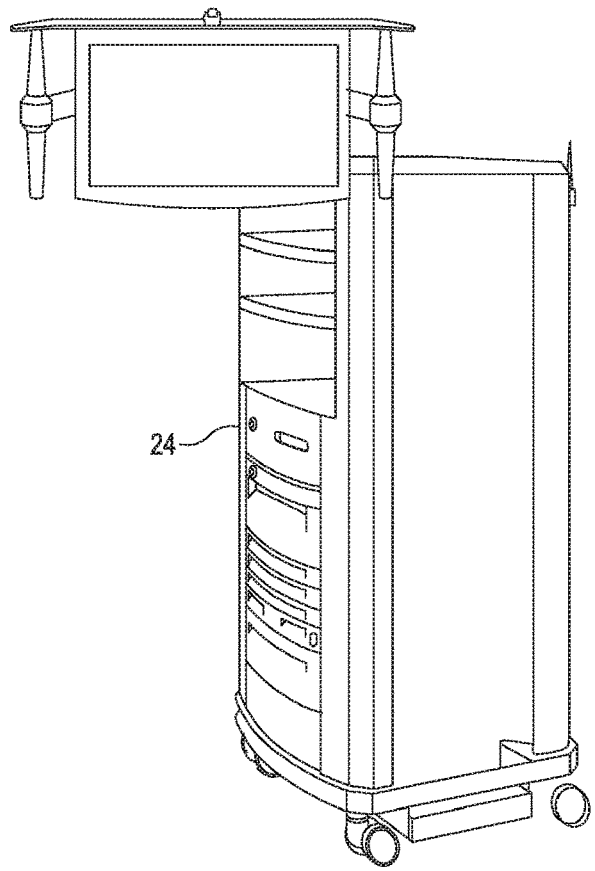
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

FIG. 5 shows a Patient Side Cart 22. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

FIG. 6 shows a robotic surgical tool 100, in accordance with many embodiments. The robotic surgical tool 100 is an example of the surgical tool 26. The surgical tool 100 includes an end effector 102, an elongated instrument shaft assembly 104, and a proximal assembly 106. The end effector 102 is supported by the instrument shaft assembly 104 at a distal end of the instrument shaft assembly 104. The proximal assembly 106 includes a proximal chassis 108 and an actuation portion 110 supported by the proximal chassis 108. The actuation portion 110 is configured to articulate actuation cables used to articulate an actuation rod assembly mounted to translate along a lumen of the instrument shaft assembly 104. The actuation rod assembly includes an actuation rod that is drivingly coupled with the end effector 102 to transfer push/pull actuation forces to the end effector 102. The push/pull actuation forces transferred to the end effector 102 can be used to actuate any suitable mechanism of the end effector 102, for example, a jaw articulation mechanism to clamp tissue, a staple deployment mechanism to deploy staples into clamped tissue, and/or a cutting mechanism to cut tissue clamped and stapled by the end effector 102.

FIG. 7A and FIG. 7B are simplified schematic diagrams illustrating the surgical tool 100. The surgical tool 100 includes a cable-driven mechanism 112 for transferring push/pull actuation force to the end effector 102. The cable-driven mechanism 112 includes an actuation rod assembly 114, a pulley assembly 116, an actuation cable 118, and an isolation tube 140. The actuation rod assembly 114 includes a shuttle 120 and an actuation rod 122 that is fixedly attached to the shuttle 120. The instrument shaft assembly 104 has a lumen 124 that extends from a proximal end 126 of the instrument shaft assembly 104 to a distal end 128 of the instrument shaft assembly 104. The instrument shaft assembly 104 is elongated along an instrument shaft axis 130. The shuttle 120 is disposed within the lumen 124 and mounted within the instrument shaft assembly 104 for translation along the lumen 124 parallel to the instrument shaft axis 130. The pulley assembly 116 includes a pulley 132 and a pulley support 134 that supports the pulley 132 and is coupled with the instrument shaft assembly 104. The actuation cable 118 is attached to the shuttle 120 at a connection 136. A first segment of the actuation cable 118 extends distally from the connection 136 to the pulley 132, is reeved around the pulley 132, extends proximally from the pulley 132 to a guide aperture 138 through a proximal portion of the shuttle 120, extends through the guide aperture 138, extends proximally from the guide aperture 138 to an isolation tube 140, extends through the isolation tube 140, extends proximally from the isolation tube 140 to a capstan 142 of the actuation portion 110, and is wrapped around the capstan 142 in a first direction. A second segment of the actuation cable 118 extends proximally from the connection 136 to the isolation tube 140, extends through the isolation tube 140, extends proximally from the isolation tube 140 to the capstan 142, and is wrapped around the capstan 142 in a second direction opposite to the first direction.

Controlled rotation of the capstan 142 is used to control translation of the shuttle 120 along the lumen 124. In the illustrated embodiment, counter-clockwise rotation of the capstan 142 pulls the first segment of the actuation cable 118 toward the capstan 142 (and accommodates distal advancement of the second segment of the actuation cable 118) thereby pulling the shuttle 120 distally toward the end effector 102. Pulling the shuttle 120 distally pushes the actuation rod 122 toward the end effector 102. For example, the capstan 142 can be rotated to advance the shuttle 120 from the proximal position illustrated in FIG. 7A to the distal position illustrated in FIG. 7B, thereby distally advancing the actuation rod 122 through an actuation stroke. In a similar manner, the capstan 142 can be rotated to retract the shuttle 120 from the distal position illustrated in FIG. 7B to the proximal position illustrated in FIG. 7A, thereby proximally retracting the actuation rod 122 through the actuation stroke. In the illustrated embodiment, the shuttle 120 has a central slot configured to accommodate the pulley assembly 116 for all positions of the shuttle 120 from the proximal position illustrated in FIG. 7A to the distal position illustrated in FIG. 7B.

The articulation of the actuation rod 122 can be used to transfer significant actuation force to the end effector 102 to actuate any suitable mechanism of the end effector 102. For example, articulation of the actuation rod 122 from the proximal position illustrated in FIG. 7A to the distal position illustrated in FIG. 7B and/or from the distal position illustrated in FIG. 7B to the proximal position illustrated in FIG. 7A can be used to articulate a jaw of the end effector to clamp tissue between the jaw and a replaceable stapler cartridge mounted to the end effector 102, articulate the stapler cartridge to deploy staples from the stapler cartridge into tissue clamped between the stapler cartridge and the jaw, and/or articulate a cutting element to cut tissue clamped between the stapler cartridge and the jaw and stapled via staples deployed from the stapler cartridge into the clamped tissue.

In many embodiments, the instrument shaft assembly 104 is mounted to the proximal assembly 106 for controlled rotation of the instrument shaft assembly 104 relative to the proximal chassis 108 around the instrument shaft axis 130. In many embodiments, the shuttle 120 is mounted within the lumen 124 to rotate with the instrument shaft assembly 104. As a result of the rotation of the shuttle 120 with rotation of the instrument shaft assembly 104, a portion of the second segment of the actuation cable 118 (extends proximally from the connection 136 to the capstan 142) and a portion of the first segment of the actuation cable 118 that extends proximally from the guide aperture 138 to the capstan 142 will inter-twist in accordance with the amount of rotation of the instrument shaft assembly 104 relative to the proximal chassis 108. In many embodiments, the isolation tube 140 is configured to enclose and/or constrain the location of at least a portion of the inter-twisted portions of the actuation cable 118. The isolation tube 140 can be used to isolate one or more other actuation members for the end effector that are disposed in the lumen 124 surrounding the isolation tube 140 from the inter-twisted portions of the actuation cable 118 to prevent the inter-twisting of the actuation cable 118 from interfering with the surrounding one or more other actuation members.

FIG. 8 through FIG. 12 illustrate an embodiment of the surgical tool 100 of FIG. 7A and FIG. 7B. FIG. 8 shows embodiments of the end effector 102, a partial view of the instrument shaft assembly 104, the proximal assembly 106, the pulley assembly 116, the shuttle 120, the actuation rod 122, and the isolation tube 140. FIG. 9 is a plan view of the embodiment of the surgical tool 100 of FIG. 8 showing a partial view of the instrument shaft assembly 104, the pulley assembly 116, the shuttle 120, the actuation rod 122, and the isolation tube 140.

Figure 10:
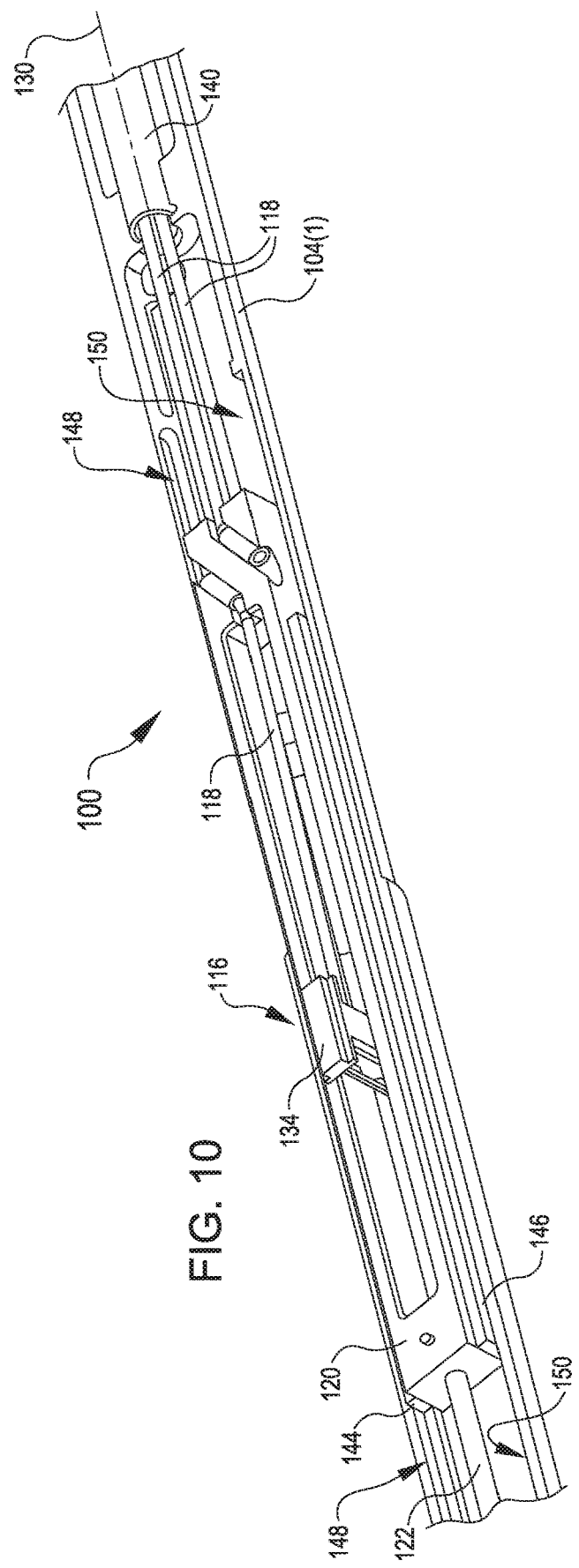
FIG. 10 is a close-up view showing components of the cable-driven mechanism for transferring push/pull actuation forces to the end effector of the surgical tool of FIG. 8.

FIG. 10 is a close-up view of the embodiment of the surgical tool 100 of FIG. 8 showing a first component 104(1) of the instrument shaft assembly 104, the pulley assembly 116, the shuttle 120, the actuation rod 122, the actuation cable 118, and the isolation tube 140. A mating second component of the instrument shaft assembly 104 is not shown in FIG. 10. In the illustrated embodiment, the instrument shaft assembly 104 includes the illustrated first component 104(1) and the mating second component of the instrument shaft assembly 104 (not shown in FIG. 10) to enable installation of the actuation rod assembly 114 (which includes the shuttle 120 and the actuation rod 122), the pulley assembly 116, the isolation tube 140, and the actuation cable 118 into the lumen 124 of the instrument shaft assembly 104. In the illustrated embodiment, the shuttle 120 includes a first guide feature 144 that protrudes in a first direction and a second guide feature 146 that protrudes in a second direction different from the first direction. In the illustrated embodiment, the second direction is in the opposite direction to the first direction. The first component 104(1) and the mating second component of the instrument shaft assembly 104 form a first slot 148 sized to accommodate the first guide feature 144 and a second slot 150 sized to accommodate the second guide feature 146 to constrain the shuttle 120 to translation along the instrument shaft axis 130 throughout the total range of movement of the shuttle 120 relative to the instrument shaft assembly 104. The first component 104(1) and the mating second component of the instrument shaft assembly 104 are also configured to enable installation of the pulley assembly 116 into the lumen 124 of the instrument shaft assembly 104. For example, the first component 104(1) and the mating second component of the instrument shaft assembly 104 can include recesses configured to receive and interface with interfacing portions of the pulley support 134, thereby capturing and restraining the pulley support 134 within the lumen 124 of the instrument shaft assembly 104. In a similar fashion, the first component 104(1) and the mating second component of the instrument shaft assembly 104 are also configured to enable installation of the isolation tube 140 into the lumen 124 of the instrument shaft assembly 104. For example, the first component 104(1) and the mating second component of the instrument shaft assembly 104 can include recesses configured to receive and interface with interfacing portions of the isolation tube 140, thereby capturing and restraining the isolation tube 140 within the lumen 124 of the instrument shaft assembly 104.

Figure 11:
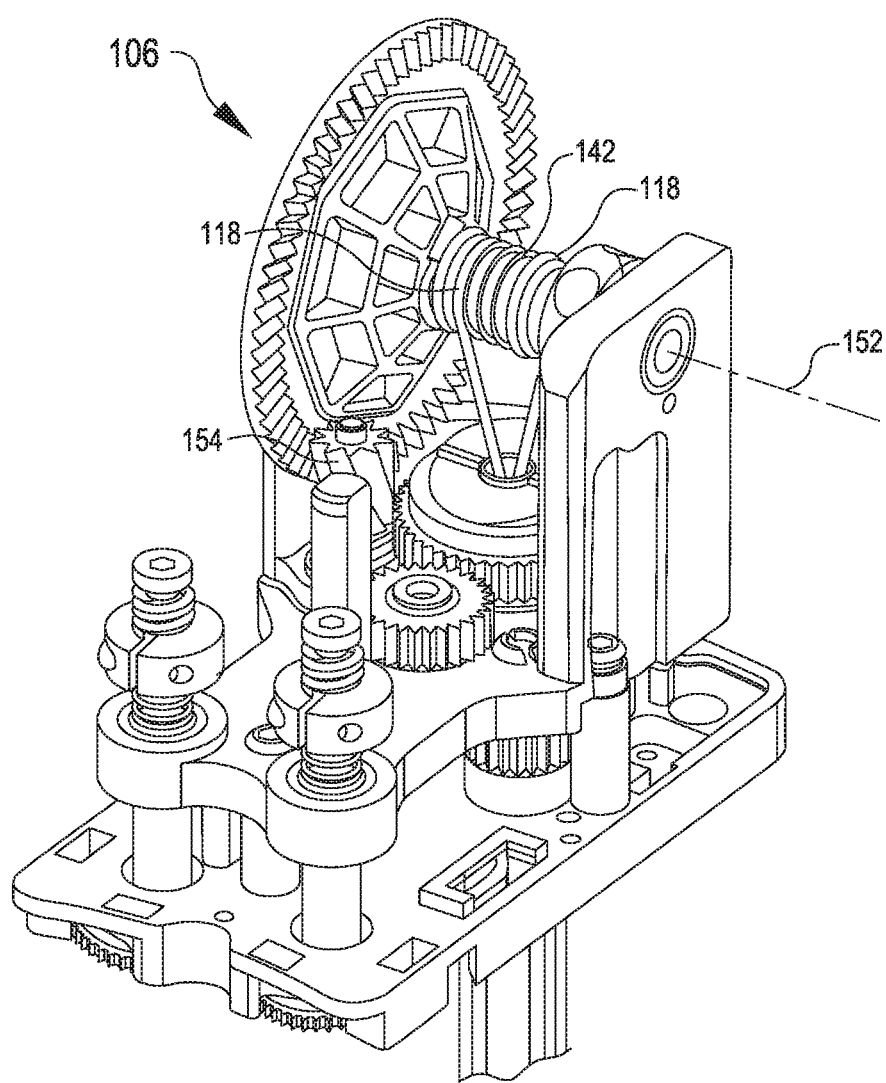
FIG. 11 and FIG. 12 are views of a proximal actuation mechanism operable to actuate the cables of the cable-driven mechanism for transferring push/pull actuation forces to the end effector of the surgical tool of FIG. 8.
Figure 12:
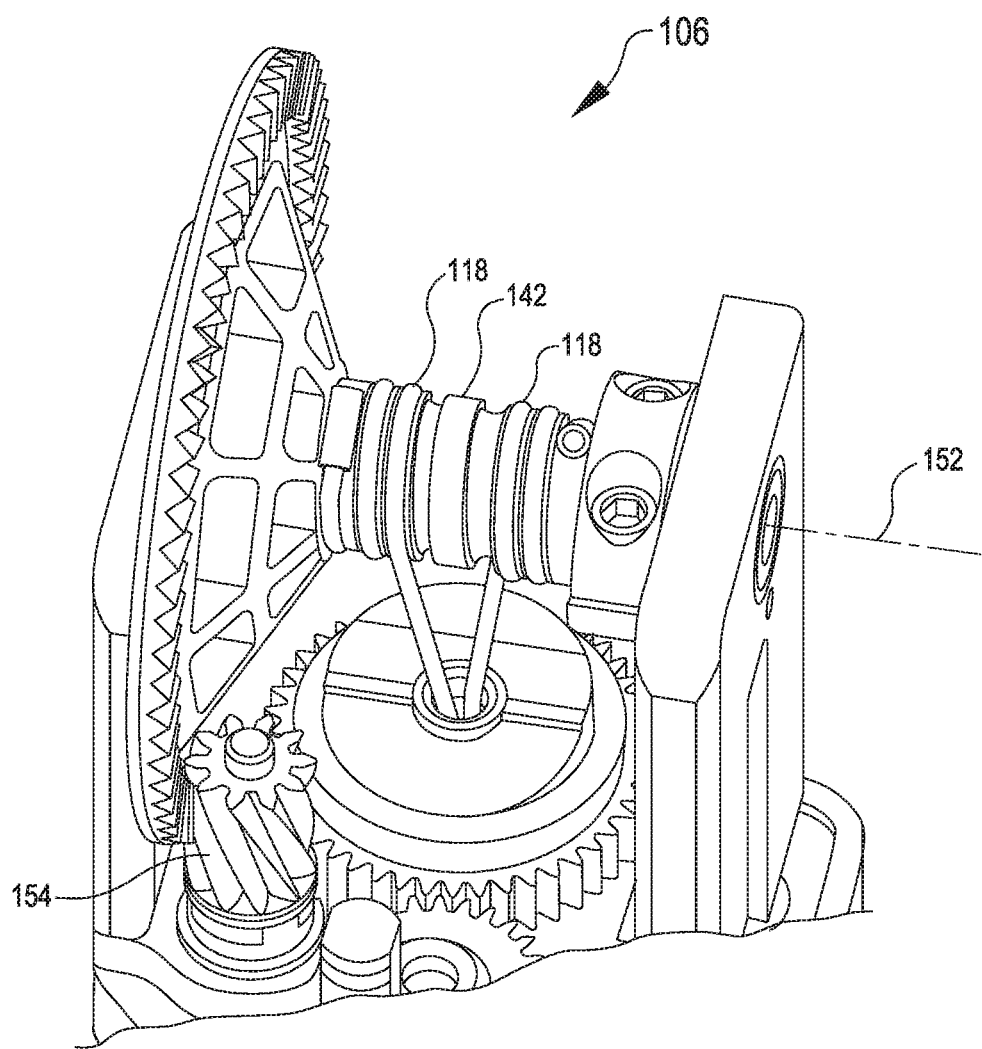

FIG. 11 and FIG. 12 are views of the proximal assembly 106 of the surgical tool 100. The actuation cable 118 is reeved around the capstan 142. The capstan 142 is mounted for rotation about a capstan axis 152 that is perpendicular to the instrument shaft axis 130. Controlled rotation of the capstan 142 via an actuation input 154 controls extension and retraction of the first and second segments of the actuation cable 118 so as to control transfer of actuation force to the end effector 102 via the actuation rod 122. In the illustrated embodiment, the capstan 142 includes an adjustment feature that is operable to adjust tension and/or remove slack from the actuation cable 118.

FIG. 13A and FIG. 13B are simplified schematic diagrams illustrating a surgical tool 200. The surgical tool 200 is similar to the surgical tool 100, but instead of including the cable-driven mechanism 112, includes a band-driven mechanism 212 for transferring push/pull actuation force to the end effector 102. The band-driven mechanism 212 includes an actuation rod assembly 214, a drive band end support 216, a drive band 218, and an isolation tube 240. The actuation rod assembly 214 includes a shuttle 220 and an actuation rod 222 that is fixedly attached to the shuttle 220. The instrument shaft 204 has a lumen 224 that extends from a proximal end 226 of the instrument shaft 204 to a distal end 228 of the instrument shaft 204. The instrument shaft 204 is elongated along the instrument shaft axis 230. The shuttle 220 is disposed within the lumen 224 and coupled with the instrument shaft 204 for translation along the lumen 224 along the instrument shaft axis 230. The drive band end support 216 includes a drive band end support frame 234 that supports a first bearing 232a and a second bearing 232b. The drive band end support frame 234 is disposed within the lumen 224 and mounted to the instrument shaft 204. The drive band 218 is attached to the shuttle 220 at a connection 236. A first segment of the drive band 218 extends distally from the connection 236 to the first and second bearings 132a, 132b, is reeved around the first and second bearings 132a, 132b, extends proximally from the first and second bearings 132a, 132b to a guide aperture through the shuttle 220 on a side of the shuttle 220 opposite to the connection 236, extends through the guide aperture, extends proximally from the guide aperture to the isolation tube 240, extends through the isolation tube 240, extends proximally from the isolation tube 240 to a capstan 242 of the actuation portion 210, and is wrapped around the capstan 242 in a first direction. A second segment of the cable 218 extends proximally from the connection 236 to the isolation tube 240, extends through the isolation tube 240, extends proximally from the isolation tube 240 to the capstan 242, and is wrapped around the capstan 242 in a second direction opposite to the first direction.

Controlled rotation of the capstan 242 is used to control translation of the shuttle 220 along the lumen 224. In the illustrated embodiment, rotation of the capstan 242 in a first direction pulls the first segment of the drive band 218 toward the capstan 242 (and accommodates distal advancement of the second segment of the drive band 218) thereby pulling the shuttle 220 distally toward the end effector 102. Pulling the shuttle 220 distally pushes the actuation rod 222 toward the end effector 102. For example, the capstan 242 can be rotated to advance the shuttle 220 from the proximal position illustrated in FIG. 13A to the distal position illustrated in FIG. 13B, thereby distally advancing the actuation rod 222 through an actuation stroke. In a similar manner, the capstan 242 can be rotated to retract the shuttle 220 from the distal position illustrated in FIG. 13B to the proximal position illustrated in FIG. 13A, thereby proximally retracting the actuation rod 222 through the actuation stroke.

The articulation of the actuation rod 222 can be used to transfer significant actuation force to the end effector 102 to actuate any suitable mechanism of the end effector 102. For example, articulation of the actuation rod 222 from the proximal position illustrated in FIG. 13A to the distal position illustrated in FIG. 13B and/or from the distal position illustrated in FIG. 13B to the proximal position illustrated in FIG. 13A can be used to articulate a jaw of the end effector to clamp tissue between the jaw and a replaceable stapler cartridge mounted to the end effector 102, articulate the stapler cartridge to deploy staples from the stapler cartridge into tissue clamped between the stapler cartridge and the jaw, and/or articulate a cutting element to cut tissue clamped between the stapler cartridge and the jaw and stapled via staples deployed from the stapler cartridge into the clamped tissue.

In the illustrated embodiment, the instrument shaft 204 is mounted to the proximal assembly 206 for controlled rotation of the instrument shaft 204 relative to the proximal chassis 208 around the instrument shaft axis 230. In many embodiments, the shuttle 220 is mounted within the lumen 224 to rotate with the instrument shaft 204. As a result of the rotation of the shuttle 220 with rotation of the instrument shaft 204, a portion of the second segment of the drive band 218 (extends proximally from the connection 236 to the capstan 242) and a portion of the first segment of the drive band 218 that extends proximally from the guide aperture in the shuttle 220 to the capstan 242 will inter-twist in accordance with the amount of rotation of the instrument shaft 204 relative to the proximal chassis 208. In many embodiments, the isolation tube 240 is configured to enclose and/or constrain the location of at least a portion of the inter-twisted portions of the drive band 218. The isolation tube 240 can be used to isolate one or more other actuation members for the end effector 102 that are disposed in the lumen 224 surrounding the isolation tube 240 from the inter-twisted portions of the drive band 218 to prevent the inter-twisting of the drive band 218 from interfering with the surrounding one or more other actuation members.

Figure 14:
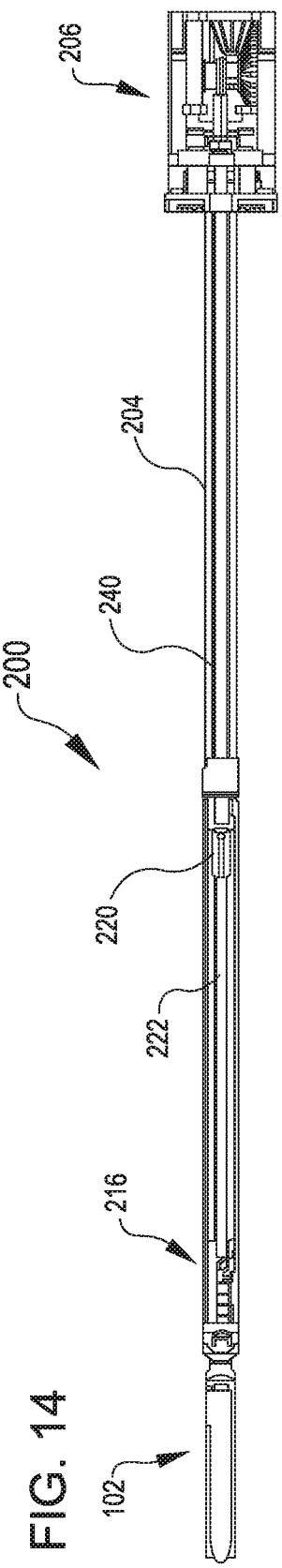
FIG. 14 is a plan view of an embodiment of the surgical tool of FIG. 13A and FIG. 13B.
Figure 15:
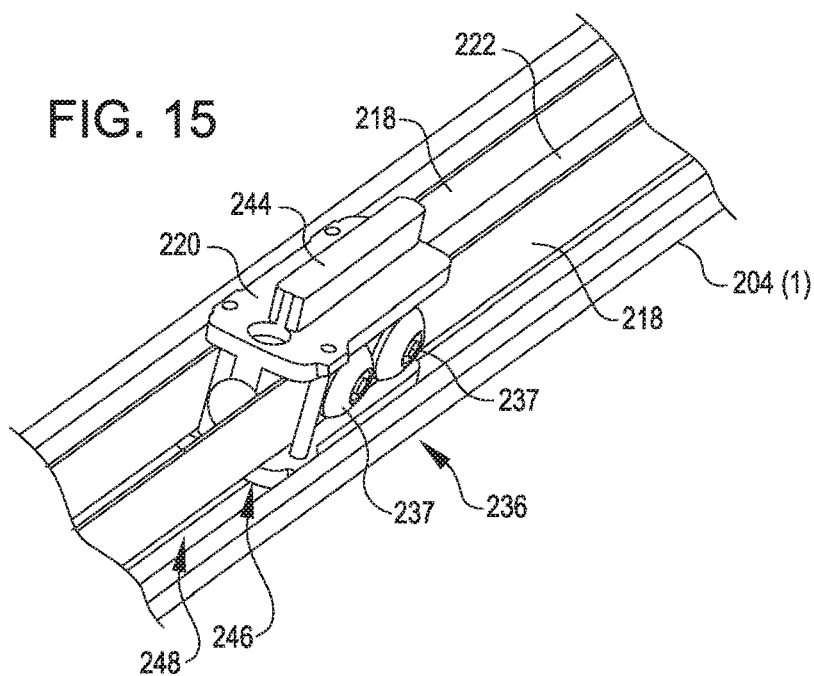
FIG. 15 and FIG. 16 are close-up views showing a band-driven shuttle of the band-driven mechanism for transferring push/pull actuation forces to the end effector of the surgical tool of FIG. 14.

FIG. 14 through FIG. 17 illustrate an embodiment of the surgical tool 200 of FIG. 13A and FIG. 13B. FIG. 14 shows embodiments of the end effector 102, the instrument shaft 204, the proximal assembly 206, the drive band end support 216, the shuttle 220, the actuation rod 222, and the isolation tube 240. FIG. 15 is close-up view showing the shuttle 220, the drive band 218, the actuation rod 222, the first component 204(1) of an instrument shaft 204 (second component 204(2) of the instrument shaft 204 not shown in FIG. 15), and the connection 236 between the drive band 218 and the shuttle 220. In the illustrated embodiment, the connection 236 includes two protruding head bolts 237 that extend through respective holes in the drive band 218 and are mated with respective threaded holes in the shuttle 220, thereby securing the local portion of the drive band 218 to the shuttle 220.

In the illustrated embodiment, the instrument shaft 204 includes the illustrated first component 204(1) and the mating second component 204(2) of the instrument shaft 204 (not shown in FIG. 15 and shown in FIG. 16) to enable installation of the actuation rod assembly 214 (which includes the shuttle 220 and the actuation rod 222), the drive band end support 216, the isolation tube 240, and the drive band 218 into the lumen 224 of the instrument shaft 204. In the illustrated embodiment, the shuttle 220 includes a first guide feature 244 that protrudes in a first direction and a second guide feature 246 (hidden from view in FIG. 15) that protrudes in a second direction different from the first direction. In the illustrated embodiment, the second direction is in the opposite direction to the first direction. The first component 204(1) of the instrument shaft 204 has a first slot 248 sized to accommodate the second guide feature 246 and the second component 204(2) has a second slot 250 sized to accommodate the first guide feature 244 to constrain the shuttle 220 to translation along the instrument shaft axis 230 throughout the total range of movement of the shuttle 220 relative to the instrument shaft 204. The first component 204(1) and the mating second component 204(2) of the instrument shaft assembly 104 are also configured to enable installation of the drive band end support 216 into the lumen 224 of the instrument shaft 204. For example, the first component 204(1) and the mating second component 204(2) of the instrument shaft 204 can include recesses configured to receive and interface with interfacing portions of a drive band end support frame 234, thereby capturing and restraining the drive band end support 216 within the lumen 224 of the instrument shaft 204. In a similar fashion, the first component 204(1) and the mating second component 204(2) of the instrument shaft 204 are also configured to enable installation of the isolation tube 240 into the lumen 224 of the instrument shaft 204. For example, the first component 204(1) and the mating second component 204(2) of the instrument shaft 204 can include recesses configured to receive and interface with interfacing portions of the isolation tube 240, thereby capturing and restraining the isolation tube 240 within the lumen 224 of the instrument shaft 204.

Figure 16:
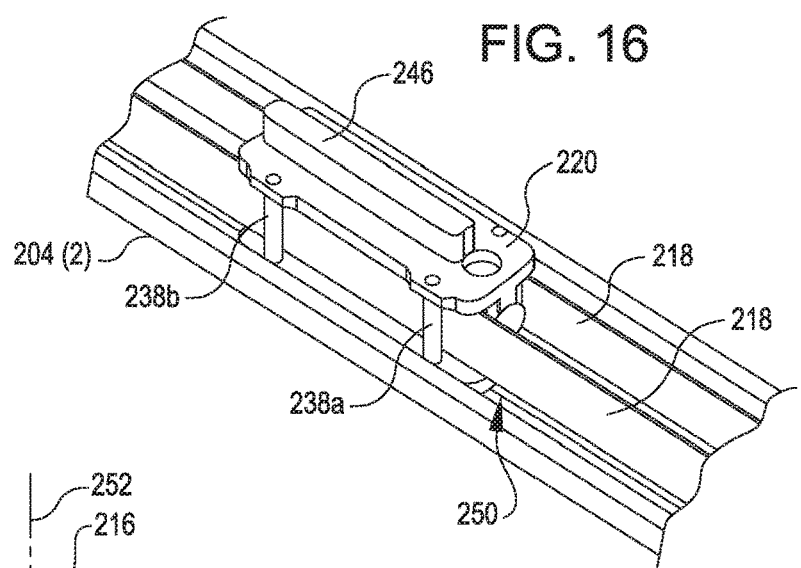

FIG. 16 is a close-up view showing the shuttle 220 and guide pins 238a, 238b that form a guide slot through which the drive band 218 extends. During actuation of the shuttle 220 via actuation of the drive band 218, the drive band 218 slides through the guide slot between the guide pins 238a, 238b and the shuttle 220. FIG. 16 also shows the second guide feature 246 and the second component 204(2) of the instrument shaft 204.

Figure 17:
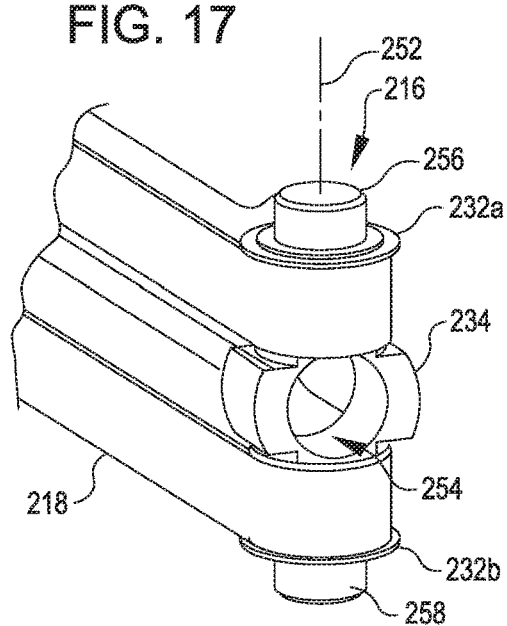
FIG. 17 is a close-up view showing a drive band end support of the band-driven mechanism for transferring push/pull actuation forces to the end effector of the surgical tool of FIG. 14.

FIG. 17 is a close-up view showing the drive band end support 216. The drive band end support 216 includes the drive band end support frame 234 and the first and second bearings 232a, 232b mounted on the drive band end support frame 234 for rotation about a drive band end support axis 252 perpendicular to the instrument shaft axis 230 and parallel to the side faces of the drive band 218. The drive band end support frame 234 has an aperture 254 sized to accommodate the actuation rod 222, which extends through the aperture 254. The drive band end support frame 234 includes first and second end journals 256, 258 that mate with complementary-shaped recesses in the instrument shaft 204 to support the drive band end support frame 234 at a fixed location within the lumen 224 of the instrument shaft 204.

Other variations are within the spirit of the present invention. For example, while five different types of stapler cartridges are described herein, any suitable number of stapler cartridge types can be employed including fewer and more than the described five stapler cartridge types. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical tool comprising:
   an actuation portion;
   an end effector;
   an instrument shaft assembly coupling the actuation portion to the end effector, the instrument shaft assembly being elongated along an instrument shaft axis and defining a lumen, the instrument shaft assembly including a guide surface disposed towards a distal end of the lumen;
   an actuation rod assembly drivingly coupled with the end effector, the actuation rod assembly being slideably mounted within the lumen for translation relative to the instrument shaft along the instrument shaft axis; and
   a flexible tension member drivingly coupling the actuation portion to the actuation rod assembly; the flexible tension member being connected to the actuation rod assembly at a connection that is longitudinally disposed between the actuation portion and the guide surface; the flexible tension member including a first portion that, from the connection, extends distally towards the guide surface, wraps around the guide surface, and extends proximally towards the actuation portion, the actuation portion being operable to increase tension in the first portion of the flexible tension member to translate the actuation rod assembly in a distal direction.

2. The surgical tool of claim 1, wherein the flexible tension member includes a second portion extending proximally through the lumen from the connection to the actuation portion, the actuation portion being drivingly coupled with the second portion and operable to increase tension in the second portion to move the actuation rod assembly in a proximal direction.

3. The surgical tool of claim 2, wherein:
the actuation portion is operable to rotate the instrument shaft assembly around the instrument shaft axis relative to a proximal chassis supporting the instrument shaft assembly;
the actuation rod assembly is constrained to rotate with the instrument shaft assembly around the instrument shaft axis; and
the surgical tool further comprises an isolation tube extending along the instrument shaft axis, the isolation tube being disposed between the connection and the actuation portion, the first and second portions of the flexible tension member passing through the isolation tube, the isolation tube enclosing an inter-twistable length of the first and second portions and isolating the inter-twistable length from a region of the lumen surrounding the isolation tube.

4. The surgical tool of claim 2, wherein:
the first portion of the flexible tension member comprises a first length of cable;
the second portion of the flexible tension member comprises a second length of cable;
the surgical tool comprises a pulley that includes the guide surface;
the actuation portion is operable to move the actuation rod assembly through a range of movement relative to the pulley; and
the actuation rod assembly comprises a slot configured to accommodate the pulley throughout the range of movement.

5. The surgical tool of claim 4, wherein the actuation rod assembly comprises a cable guide aperture through which the second length of cable extends.

6. The surgical tool of claim 1, wherein the instrument shaft assembly comprises a first component and a second component, the first and second components being configured to accommodate insertion of the actuation rod assembly, the guide surface, and the flexible tension member into the lumen when the first and second components are uncoupled, the first and second components being configured to be joined to form the lumen.

7. The surgical tool of claim 6, wherein:
the actuation portion is operable to move the actuation rod assembly through a range of movement relative to the guide surface;
the actuation rod assembly comprises a first guide feature that protrudes in a first direction and a second guide feature that protrudes in a second direction different than the first direction; and
the first component and the second component form a first slot sized to accommodate the first guide feature and a second slot sized to accommodate the second guide feature throughout the range of movement.

8. The surgical tool of claim 1, wherein:
the flexible tension member comprises a drive band; and
the drive band comprises a slot through which a portion of the actuation rod assembly between the connection and the end effector extends.

9. The surgical tool of claim 8, comprising:
a support frame having an aperture through which the portion of the actuation rod assembly between the connection and the end effector extends;
a first bearing mounted to the support frame to rotate around a guide surface axis perpendicular to the instrument shaft axis and interface with the drive band on a first side of the slot; and
a second bearing mounted to the support frame to rotate around the guide surface axis and interface with the drive band on a second side of the slot opposite to the first side of the slot,
wherein the first and second bearings include the guide surface.

10. The surgical tool of claim 8, wherein the actuation rod assembly comprises a drive band guide aperture through which the drive band extends.

11. A method for actuating an end effector of a surgical tool, the method comprising:
supporting an end effector via an instrument shaft assembly elongated along an instrument shaft axis;
enclosing an actuation rod assembly within a lumen of the instrument shaft assembly;
guiding the actuation rod assembly during movement of the actuation rod assembly along the instrument shaft axis; and
operating an actuation portion to increase tension in a first portion of a flexible tension member drivingly coupled with the actuation rod assembly to move the actuation rod assembly in a distal direction to actuate the end effector, the first portion of the flexible tension member extending distally from the actuation portion to a guide surface, wrapped around the guide surface, and extending from the guide surface to a connection between the first portion of the flexible tension member and the actuation rod assembly.

12. The method of claim 11, further comprising operating the actuation portion to increase tension in a second portion of the flexible tension member drivingly coupled with the actuation rod assembly to move the actuation rod assembly in a proximal direction.

13. The method of claim 12, further comprising:
operating the actuation portion to rotate the instrument shaft assembly around the instrument shaft axis relative to a proximal chassis supporting the instrument shaft assembly;
constraining the actuation rod assembly to rotate with the instrument shaft assembly around the instrument shaft axis; and
enclosing an inter-twistable length of the first and second portions of the flexible tension member disposed between the actuation rod assembly and the actuation portion within an isolation tube to isolate the inter-twistable length from a region of the lumen surrounding the isolation tube.

14. The method of claim 12, wherein:
the first portion of the flexible tension member comprises a first length of cable;
the second portion of the flexible tension member comprises a second length of cable;
the surgical tool comprises a pulley; and
the method further comprises:
operating the actuation portion to move the actuation rod assembly through a range of movement relative to the pulley; and
accommodating the pulley within a slot of the actuation rod assembly throughout the range of movement.

15. The method of claim 14, further comprising guiding the second length of cable via a cable guide aperture in the actuation rod assembly through which the second length of cable extends.

16. The method of claim 11, further comprising:

inserting the actuation rod assembly, the guide surface, and the flexible tension member into a first component of the instrument shaft assembly; and coupling a second component of the instrument shaft assembly to the first component to enclose the actuation rod assembly, the guide surface, and a portion of the flexible tension member within the lumen of the instrument shaft assembly.

17. The method of claim 16, further comprising:

operating the actuation portion to move the actuation rod assembly through a range of movement relative to the guide surface; and interfacing protruding guide features of the actuation rod assembly with the instrument shaft assembly to guide movement of the actuation rod assembly relative to the instrument shaft assembly through the range of movement.

18. The method of claim 11, wherein the flexible tension member comprises a drive band, the method further comprising accommodating a portion of the actuation rod assembly between the connection and the end effector through a slot in the drive band.

19. The method of claim 18, further comprising:

accommodating a portion of the actuation rod extending between the connection and the end effector in an aperture of a support frame;

supporting a first bearing mounted to the support frame to rotate around a guide surface axis perpendicular to the instrument shaft axis and interface with the drive band on a first side of the slot; and supporting a second bearing mounted to the support frame to rotate around the guide surface axis and interface with the drive band on a second side of the slot opposite to the first side of the slot, wherein the first and second bearings include the guide surface.

20. The method of claim 18, further comprising guiding the drive band via a drive band guide aperture of the actuation rod assembly through which the drive band extends.

* * * * *